Figure 1:
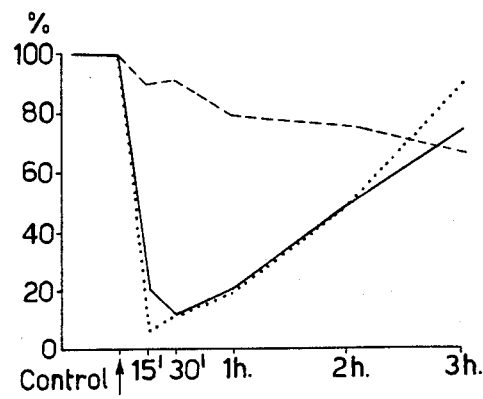

United States Patent [19]

Ferrari et al.

[11] Patent Number: 4,683,245
[45] Date of Patent: Jul. 28, 1987

[54] LAEVOROTATORY ANTIPODE OF MOPROLOL AS AN ANTIHYPERTENSIVE

[75] Inventors: Giorgio Ferrari; Vittorio Vecchietti, both of Milan, Italy

[73] Assignee: SIMES S.p.A. Societa Italiana Medicinali e Sintetici, Milan, Italy

[21] Appl. No.: 434,362

[22] Filed: Oct. 14, 1982

Related U.S. Application Data

[63] Continuation-in-part of Ser. No. 371,428, Apr. 23, 1982, abandoned, which is a continuation of Ser. No. 123,770, Feb. 20, 1980, abandoned.

[30] Foreign Application Priority Data

Mar. 1, 1979 [IT] Italy .............................. 20671 A/79

[51] Int. Cl.$^4$ .............................................. A61K 31/135
[52] U.S. Cl. ................................... 514/652; 564/349
[58] Field of Search ......................... 424/330; 514/652

[56] References Cited

U.S. PATENT DOCUMENTS

| | | | |
|---|---|---|---|
| 3,432,545 | 3/1969 | Howe | 260/501.17 |
| 3,483,221 | 12/1969 | Wilhelm et al. | 424/280 X |
| 3,501,769 | 3/1970 | Crowther et al. | 424/250 X |
| 3,538,150 | 11/1970 | Gilman et al. | 260/501.17 |
| 3,649,691 | 3/1972 | Shavel et al. | 564/349 |
| 3,911,136 | 10/1975 | Ferrari | 424/330 |
| 4,131,686 | 12/1978 | Ikezaki et al. | 424/330 |

OTHER PUBLICATIONS

Ferrini, R., et al., *Arzneim.-Forsch.*, 20(8), 1074–1079 (1970).
Burger, A. (Editor), *Medicinal Chemistry*, 3rd Edition, Interscience, New York, 1970, pp. 1052–1055.

*Primary Examiner*—Richard A. Schwartz
*Attorney, Agent, or Firm*—Cushman, Darby & Cushman

[57] ABSTRACT

This invention relates to a process for the separation of moprolol into its two optical antipodes, substantially characterized by the fact of salifying racemic moprolol with L(+)glutamic acid; treating the thus obtained mixture of diastereoisomeric salts with a water/alcohol mixture, in this way separating the L(+)glutamate insoluble salt of (+)moprolol; treating the resultant mother liquors which contain in solution the L(+)glutamate salt of (−)moprolol with a base so as to separate the laevorotatory isomer of crystalline moprolol, which finally undergoes a purification. The invention also relates to a pharmaceutical composition containing said laevorotatoryisomer of moprolol.

3 Claims, 4 Drawing Figures

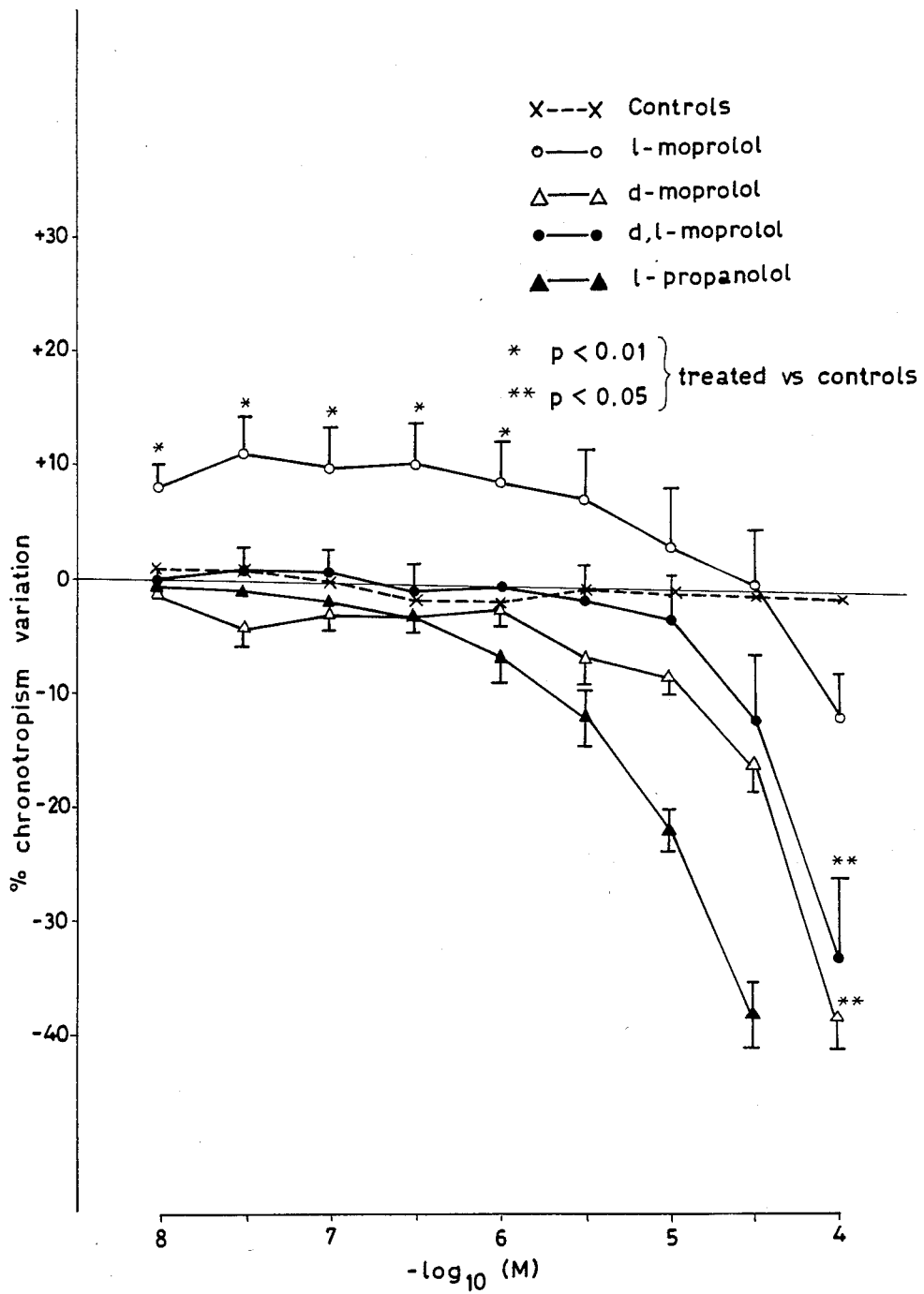

LAEVOROTATORY ANTIPODE OF MOPROLOL AS AN ANTIHYPERTENSIVE

This is a continuation-in-part of application Ser. No. 371,428, filed Apr. 23, 1982, now abandoned, which in turn is a continuation of Ser. No. 123,770, filed Feb. 20, 1980, now abandoned.

The present invention relates to a novel method of separation of racemic moprolol into its optical antipodes, of which latter a physico-chemical characterization is furthermore given, and to the corresponding pharmaceutical compositions which contain the pure laevorotatory isomer, of which a pharmacological spectrum has also been defined in comparison with the racemic form and the dextro-rotatory antipode.

Moprolol, which is chemically 1-(o-methoxy-phenoxy)-3-isopropyl-amino-propane-2-ol (U.S. Pat. No. 3,911,136) is a beta-blocking agent which is endowed with outstanding pharmacological properties. It is a racemic compound which has an asymmetric carbon atom in its basic side chain, such atom being marked by an asterisk in formula (I) and giving rise to the possibility of having two optical antipodes, the laevorotatory and the dextrorotatory:

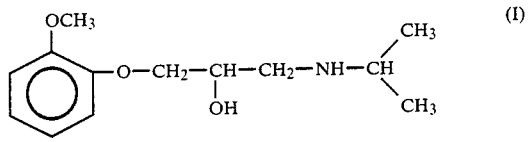

(I)

Beta-blocking agents, generally speaking, are a class of chemical compounds of outstanding pharmacological and clinical importance (Ann. Rep. Med. Chemistry, 10, 51, 1975).

Their employment in human therapy includes the treatment of cardiac diseases (angina pectoris, myocardial infarction, arrhythmia), vascular diseases (hypertension), psychic illness (anxiety, essential tremor, schizophrenia).

It is well known that the pharmacological activity of such types of substances is directly correlated with their beta-blocking activity, that is their ability to block the beta-receptors, by occuping them instead of the physiological adrenergic amines, in all those pharmacological or pathological cases characterized by an excess of adrenergic activity.

It is also known (Nature, 210, 1335, 1966; Il Farmaco, Ed. Sci., 21, 299, 1966) that the beta-blocking activity of such substances is generally entirely ascribable to the laevorotatory form of said substances while the dextrorotatory form seems to be devoid of activity, or at least to be of very low activity.

It is, finally, known that in human therapy the beta-blocking agents should be administered in sufficient dosages and amounts to maintain the beta-block for 24 hours, and that such treatment should be prolonged for extended periods of time. Hence it follows that toxic side effects may appear such as cardiotoxicity, which is ascribable to an aspecific depressant action on the myocardial membrane, and bronchial constriction.

The maintaining of an unchanged activity and at the same time halving the therapeutical dose of such drugs and subsequently greatly reducing the toxicological effects would be a cause of real clinical progress.

A first aim of the present invention is therefore to provide a method for the separation of the optical antipodes of moprolol such as to obtain the dextrorotatory and the laevorotatory isomer with an elevated degree of optical purity.

A further aim of the invention is the preparation of moprolol-based compositions characterized by a beta-adrenergic receptor blocking activity, such as call for a therapeutic dose of active ingredient that is very considerably lower than that of compositions of racemic moprolol, in this way greatly reducing any possible toxicological risk resulting as side effect of prolonged administration thereof.

In this regard it has now been surprisingly found, and this represents one of the aspects of the present invention, that the activity of the laevoratatory isomer of moprolol is exactly double that of racemic moprolol, while the activity of the dextro-rotatory isomer is practically nil. It has been proved that the unexpected and surprising good tolerability of the laevorotatory isomer of moprolol is due to the fact that it is endowed with a cardiac stimulant action whereas the racemic moprolol is endowed with a cardiac depressant action.

From this it follows, for the reasons heretofore set out, that the clinical use of laevorotatory moprolol would make possible dosages half as large as those required for the racemic form, with identical therapeutic effect and unexpected fewer toxicological effects. This is particularly advantageous in the therapeutic treatment of certain diseases which draw evident advantage from treatments with beta-blocking drugs, which are however necessary in continued and high doses. Particularly reference is made to hypertension, angina pectoris and certain types of anxiety state.

To achieve the aims described above, the present invention proposes a process for the separation of moprolol into its two optical antipodes, such process being substantially characterized by the salification of racemic moprolol with L(+)glutamic acid; by treating the thus obtained mixture of diastereoisomeric salts with a water/alcohol mixture, in this way separating the L(+)glutamate salt of crystalline (+)moprolol; by treating the resultant mother liquors, after their purification, with a base in aqueous solution to give (−)moprolol base, which is finally purified to a high degree of optical purity.

A preferred process according to the invention provides for salifying the racemic moprolol with an equimolecular quantity of L(+)glutamic in an alcohol/water mixture and, after solvent evaporation, obtaining the mixture of the two optically active salts. This mixture is treated with an appropriate quantity of isopropanol/methanol/water in the ratio 80/15/5 and yields a crystalline solid consisting of practically pure L(+)glutamic (+) moprolol salt. The mother liquors of crystallization, brought to dryness and taken up with a mixture of i-PnOH/MeOH in a 95/5 ratio, yield after filtration of the insoluble portion a solution containing the non-crystalline L(+)glutamic(−)moprolol salt practically alone, this salt being considerably more soluble in these solvents than the corresponding crystalline L(+)glutamic(+)moprolol salt.

By evaporation of the solvent there is obtained an oil which, after treatment with bases selected among NH$_4$OH, NaHCO$_3$K$_2$CO$_3$, NaOH, KOH etc. in aqueous solution, provides the laevororatory isomer in crystalline form.

One recrystallization from ethyl acetate gives a product with an optical purity >96%. A further optical purification is obtained by converting said 96% base into the corresponding hydrochloride with gaseous HCl in solvents selected among diethyl ether, acetone, ethyl acetate, or more conveniently by means of the following method which is suitable for preparation on industrial scale. By dissolving an amount of base (5-10 kg) in 5-10 parts of chloroform and adding an equivalent amount of aqueous concentrated HCl, a solution is obtained which, when dried over $Na_2SO_4$ and evaporated to dryness under vacuum, gives the crystalline hydrochloride of (−)moprolol. A crystallization from absolute EtOH/EtOAc in the ration 10/90, or EtOH 95°/EtOAc 5/95 gives rise to the laevorotatory moprolol hydrochloride with an optical purity higher than 99%, which does not increase after subsequent and repeated crystallizations. The same operations applied to L(+)moprolol(+)glutamate gives the dextro-rotatory isomer of moprolol with and optical purity which is again >99%. The specific optical rotation of the two antipodes are respectively:

(−)moprolol hydrochloride $[\alpha]-16,8\pm0,2$ (c=5 absolute EtOH)

(+)moprolol hydrochloride $[\alpha]+17,0\pm0,2$ (c=5 absolute EtOH)

Thus, in broad outline, the process for the separation of the optical antipodes of moprolol according to the invention is carried out by employing (+)glutamic acid. In fact, it has been found that moprolol glutamate can be easily separated by crystallization into its antipodes; L(+)moprolol(+)glutamate and L(−)moprolol(+)-glutamate.

The salt containing the laevorotatory antipode is the more soloble and therefor it remains in the mother liquors from which the dextro-rotatory antipode has separated in the solid state. By evaporating the solvent the laevorotatory antipode is obtained as a salt of glutamic acid. The laevorotatory base, in its turn, is obtained by removing the slot according to known methods. The laevorotatory isomer is finally crystallized from a solvent such as ethyl acetate. Subsequently the base is converted into hydrochloride, inasmuch as the laevorotatory base obtained from the hydrochloride possesses an absolute optical purity.

In order better to describe the method according to the present invention, an example of realization is reported below which in any case is not to be considered as limiting the scope of the invention.

EXAMPLE 1

9.45 kg of racemic moprolol base, dissolved in 20 liters of methanol, were added to a suspension of 6 kg of L(+)glutamic acid $[\alpha]=+29$ (c=1 HCl 6N) in 16.5 liters of $H_2O$. The mixture was stirred at 50° C. to complete dissolution, then concentrated to dryness in vacuo. The semi-solid residue was dissolved in 20 liters of methanol/water 3/1, then diluted with 80 liters of isopropanol.

The whole was left at 4° C., after which 7.8 kg of L(+)moprolol(+)-glutamate salt crystallized which was then filtered off.

The mother liquors were then again concentrated to dryness and the residue was treated with 10 liters of isopropanol/methanol 95/5. The insoluble portion (0.5 kg) was filtered off and the filtrate was concentrated to dryness; the residue was dissolved in 15 litres of $H_2O$, cooled to 0° C. and treated with 40% NaOH to pH 12. The crystallized solid formed by (−)moprolol base, after a suitable period in a refrigerator was centrifuged, washed with water and dried to constant weight: 4.3 kg $[\alpha]-4°\pm0,2$ (c=5 absolute ethanol).

By crystallization from ethyl acetate, 3.5 kg of laevorotatory moprolol were obtained, m.p. 78°-80° C. $[\alpha]=-5,5\pm0,2$ (c=5 EtOH). The crystallized product (3.5 kg) was dissolved in 15 liters of chloroform and treated under stirring with 1,28 liters of 36% HCl. The water was separated and then 2,5 kg of $Na_2SO_4$ were added, then it was filtered and concentrated to dryness. The solid residue was crystallized from 28 liters of ethyl acetate/95° EtOH 9/1 thus obtaining 3.8 kg of (−)moprolol hydrochloride, m.p. 124°125° C. $[\alpha]-16,8\pm0,2$ (c=5 absolute EtOH).

8.3 kg of (+)moprolol L(+)glutamate were twice crystallized from $IsOH/MeOH/H_2O=60/30/10$ thus obtaining 6.6 kg of the salt, m.p. 173°-174° C. $[\alpha]+7$ (c=1 MeOH).

A suspension of 6.5 kg of salt in 20 liters of water and 10 liters of chloroform was alkalinized at 10° C. with 40% NaOH. The organic phase was separated, washed with water, dried and concentrated. The solid residue after crystallization from ethyl acetate gave 3.25kg of (+)moprolol, m.p. 78°-80° C. $[\alpha]=5,75\pm0,2$ (c=5 absolute EtOH).

Such product, converted to hydrochloride and crystallized from ethyl acetate/ethyl alcohol as for the corresponding laevorotatory isomer, gave rise to a producy of the following characteristics: m.p. 124°-125° C. $[\alpha]=17,0\pm0,2$ (c=5 absolute EtOH).

A further aspect of the present invention is to provide for pharmaceutical compositions, particularly active as beta-adrenergic receptor blocking agents, characterized by the fact of containing as active principle the pure laevorotatory antipode of moprolol.

The (−)moprolol base can be converted into an acceptable salt for therapeutical employment by treatment according to known methods with inorganic or organic salts which are suitable for such preparations. (−)moprolol hydrochloride $(C_{13}H_{21}NO_3 \cdot HCl)$ has m.p. 124°-125° C.

For a therapeutical employment, (−)moprolol hydrochloride can be formulated as tablets, sugar- or film-coated tablets, beads, solutions for drops, vials, suppositories, eye salve, hard or soft gelatin capsules, both long-acting and normal-acting, in single doses of from 5 to 250 mg.

The dosage forms realized according to pharmaceutical techniques are produced with the aid of suitable known excipients or accessories.

In this regards, description is given below of two examples of realization of pharmaceutical dosage forms according to the invention, which are not however to be considered limiting.

EXAMPLE 2

A mixture of 375 g of laevorotatory moprolol hydrochloride, 775 g of starch, 1200 g of microcrystalline cellulose and 100 g of talc was sieved, then carefully mixed with 800 ml of double distilled water. The resultant mixture was granulated, then oven-dried for 12 hours at 50° C. After sieving through a narrow-mesh screen, the dry granulated had magnesium stearate (2% over total weight) added to its, was thoroughly blended and compressed into 500 mg tablets, each containing 75 mg of active ingredient.

EXAMPLE 3

15 g of laevorotatory moprolol hydrochloride was separately dissolved in approximately 2 liters of double distilled water, and 48 g of sodium chloride in approximately 2 liters of double distilled water. The two solutions were combined and 60 ml of Esteril 10% was slowly added to them under stirring. The whole was then made to 6000 ml with double distilled water and aseptically filtered. The filtered solution was filled under an atmosphere of nitrogen into yellow-glass vials in the measure of 2 ml each. Each vial thus contained 5 mg of active ingredient. The vials were then sterilized in autoclave for 30 minutes at 110° C.

In order better to clarify the advantages connected with the use of pharmaceutical compositions according to the present invention, the attached drawings include three diagrams relating to certain experiments conducted in anesthetized dogs. These diagrams concern the inhibition by recemic moprolol, it laevorotatory optical isomer and its dextro-rotatory optical isomer, of certain homodynamic effects due to stimulation of the adrenergic beta-receptors following on intravenous infusion of isoproterenol at a dose of 0.25 μg/Kg/minute.

FIG. 1 shows the increase in heart rate due to administration of isoproterenol at the aforesaid dose, after duodenal administration of racemic moprolol (dotted line curve) at a dose of 0.5 mg/kg, of laevorotatory moprolol (continuous curve) at a dose of 0.25 mg/kg and of dextro-rotatory moprolol (dashed line curve) at a dose of 0.25 mg/kg.

Figure 2:
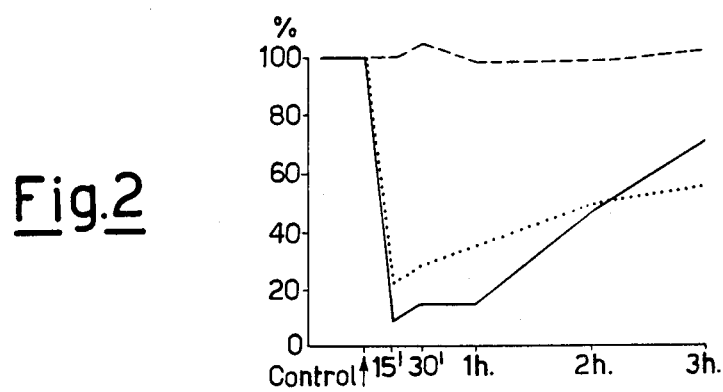
Figure 3:
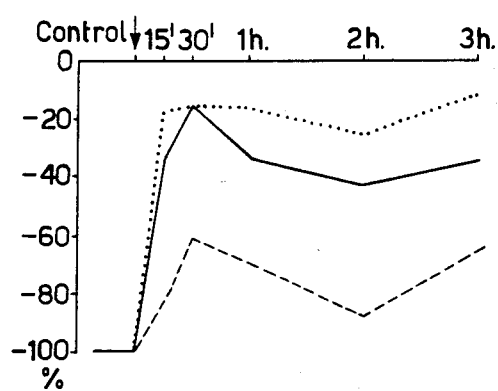

Similarly, diagram of FIG. 2 shows the increase of the hemodynamic parameter dP/dt and diagram of FIG. 3 shows the decrease of diastolic arterial pressure, again after administration of isoproterenol at the above-identified dose and after administration of racemic moprolol and its pure optical isomers according to the aforesaid doses. The curves therein reported refer to the means of the results of three tests for each substance.

As can be seen by examining said diagrams, the inhibiting activity on the above-indicated hemodynamic effects, due to the stimulation of the beta-adrenergic receptors effected by isoproterenol, is particularly evident for the laevorotatory form in a dose-dependent manner, and with a highly significant correlation coefficient ($P<0.01$) at the doses of 0.25, 0.0625 and 0.125 mg/kg of laevorotatory moprolol.

As regards the administration of the racemic form of moprolol, nearly the same effects as indicated above, with the same significance, become evident at exactly doubled doses, namely 0.5 mg/kg, as can be seen from the diagrams, 0.125 and 0.25 mg/kg respectively.

There can also be seen from the attached diagrams the almost complete lack of beta-blocking activity on the part of the dextrorotatory optical isomer.

The observation made on the beta-blocking activity possessed by laevorotatory moprolol as compared with the lack of activity of its dextro-rotatory isomer should not be seen separately from an evaluation of the toxicity of the said compounds. In this regard the following Table I reports the $LD_{50}$ of the single isomers and of the racemic product.

TABLE I

| Compound | Lethal Dose$_{50}$ ($LD_{50}$) in the mouse |
|---|---|
| Moprolol (±) | 712 mg/kg weight animal |
| Moprolol (−) | 605 mg/kg weight animal |
| Moprolol (+) | 720 mg/kg weight animal |

The data given in Table I evidence similar toxicity of the three different compounds. However, and as is known, for an exact evaluation of the activity of a drug its intrinsic toxicity has to be seen in relation to the activity demonstrated, i.e. the median effective dose ($ED_{50}$).

In this regard the following Table II gives the respective data for the three compounds (±); (−); (+).

TABLE II

| Compound | Median effective Dose ($ED_{50}$) dog |
|---|---|
| Moprolol (±) | 0.150 mg/kg weight animal |
| Moprolol (−) | 0.0781 mg/kg weight animal |
| Moprolol (+) | nil |

The data given above very clearly express the relationship existing between the doses employed, which demonstrate the activity of laevorotatory moprolol as compared with the racemic and dextro-rotatory forms.

There is no doubt that the most advantageous effective dose is the one relating to laevorotatory moprolol (0.0781 mg/kg weight animal), whereas to obtain the same response with the racemic product 0.150 mg/kg weight animal is required.

The dextro-rotatory moprolol shows the same toxicity as the laevorotatory isomer and the racemic form, but without any activity whatsoever. It therefore appears evident that the effective dose of laevorotatory moprolol is 2 times more active, inasmuch as it is 2 times smaller, than that expressed by the racemic form.

EXAMPLE 4

Experiments were carried out on spontaneously beating right atrium preparations taken from the hearts of guinea-pigs of both sexes, weighing 300 to 400 g.

Twenty hrs before sacrifice the animals were injected intramuscularly with reserpine dissolved in 20% ascorbic acid in 2 doses of 2 mg/kg each at 24 hrs distance. An equal number of animals received the reserpine solvent only and were kept as controls.

The preparations were suspended in 10 ml vessels containing Krebs-Henseleit solution aerated with 5% $O_2$ and 95% $CO_2$ and maintained at a temperature of 35° C.

The right atria were fixed to the vessel base by one end and connected to a transducer of a semiisometric microdynanometer (Basile) by the other end.

Heart rate was recorded directly from the tracing.

All the preparations were subjected to a reset traction of 0.6–0.8 g and allowed to stabilize for 1 hr before starting experiments.

The substances were placed in the vessel in cumulative concentrations. Each concentration was increased by three times as compared with the previous one and a 10 min. interspace was left between concentrations.

The control preparations were made by replacing in the vessel the only solvent ($H_2O$) in the same volumes as for the drug solutions. The effect excerted by the drug and the solvent on atrial rate was evaluated as per-cent variation as compared with baseline values.

The significance of the differences between treated and control animals was assessed by Dunnett's test.

Table III and FIG. 4 show the effects obtained on chronotropism with laevorotatory isomer, dextro-rotatory isomer and the mixture thereof.

The results achieved with the control drugs (laevorotatory isomer of propanolol and tyramine) are also reported.

It is observed that:

(A) Tyramine is devoid of positive chronotropic effect. Thus, the preparations may be regarded as depleted of catecholamines.

(B) Laevorotatory isomer of moprolol causes a stimulant effect on atrial rate in a concentration range of $1 \times 10^{-8}$ to $1 \times 10^{-6}$ M.

The curves express the average ± S E of per-cent heart rate variations as compared with baseline values.

The number of experiments performed for each drug are in brackets. The concentration effect curves of l-moprolol are also reported.

It is thus clear that the pharmaceutical compositions based on laevorotatory moprolol proposed by the present invention make it possible advantageously to achieve the purpose, initially set, of accompanying and elevated beta-blocking activity by a considerable reduction of the risk of toxic side effect (cardiac depression and bradichardia which might derive from a prolonged administration). This side effect being a specific contraindication in a number of hypertensive patients who need to be treated with beta-blocking agents.

TABLE III

RESERPINIZED GUINEA-PIG RIGHT ATRIUM

Chronotropic effect (% variation - ±S.E.)

| DRUG | No. prep. | $1 \times 10^{-8}$ | $3 \times 10^{-8}$ | $1 \times 10^{-7}$ | $3 \times 10^{-7}$ | $1 \times 10^{-6}$ | $3 \times 10^{-6}$ | $1 \times 10^{-5}$ | $3 \times 10^{-5}$ | $1 \times 10^{-4}$ |
|---|---|---|---|---|---|---|---|---|---|---|
| l-moprolol | 5 | +8.2 ± 1.82* | +11.4 ± 3.07* | +10.4 ± 3.20* | +10.4 ± 3.20* | +8.8 ± 3.63* | +7.8 ± 4.01 | +4 ± 4.99 | +0.2 ± 4.98 | −10.8 ± 4.03 |
| d-moprolol | 4 | −1.25 | −4 ± 1.68 | −2.7 ± 1.03 | −2.7 ± 1.03 | −2 ± 1.22 | −6 ± 1.87 | −7.25 ± 1.44 | −14.7 ± 2.66 | −37.5 ± 2.40** |
| d,l-moprolol*** | 4 | 0 | +1.2 ± 2.1 | +1.2 ± 2.1 | −0.25 ± 2.4 | 0 ± 0 | −1 ± 3.5 | −2.5 ± 4.3 | −11 ± 5.6 | −32 ± 6.77** |
| l-propanolol | 4 | −0.5 ± 1.66 | −0.75 ± 3.09 | −2 ± 2.8 | −3.5 ± 1.44 | −5.7 ± 1.97 | −11.2 ± 2.06 | −21.5 ± 1.19 | −37 ± 2.56 | atr. block 4/4 |
| Tyramine HCl | 5 | — | — | 0 | 0 | 0 | 0 | −1 ± 1 | −3 ± 1.4 | −3 ± 1.4 |
| Controls | 4 | +1.5 | +1.2 ± 2.3 | 0 | −1.5 ± 2.6 | −1.5 ± 1.9 | −1 ± 1.9 | −0.2 ± 0.2 | −1 ± 2.9 | −1 ± 2.9 |

*p <0.05 } treated vs controls
**p <0.01

***In order to be able to compare the effect of combined doses of the enantiomers with those of equal doses of the single enantiomers racemic moprolol was used in concentration double with respect to the single enantiomers.

(C) Dextro-rotatory isomer of moprolol induce no stimulant effect in a range of concentrations which have proved to be active for laevorotatory isomer of moprolol. On the contrary, they give rise to a depressant effect.

(D) The experiment performed with racemic moprolol showed that the dextro-rotatory isomer suppress the cardiac stimulant effect of the laevorotatory isomer.

(E) Laevorotatory isomer of propanolol evokes no stimulant effect but a depressant effect starting from a concentration of $1 \times 10^{-6}$ M. The depressant effect of laevorotatory isomer of propanolol is more marked than that evoked by laevorotatory isomer, dextro-rotatory isomer and racemic moprolol.

FIG. 4 shows the effect of laevorotatory isomer, dextro-rotatory isomer and of their mixture on spontaneously beating right atria from reserpinized guinea-pigs.

What we claim is:

1. A pharmaceutical composition for treating hypertension without causing cardiac depression which comprises a therapeutically effective amount of the laevorotatory form of moprolol or of a pharmaceutically acceptable salt thereof together with a pharmaceutically acceptable carrier.

2. A pharmaceutical composition for treating hypertension without causing cardiac depression which comprises from 5 to 250 mg of the laevorotatory form of moprolol or of a pharmaceutically acceptable salt thereof together with a pharmaceutically acceptable carrier.

3. A method for a long-term treatment of hypertension comprising administering to a hypertensive patient requiring said treatment an effective amount of the laevorotatory form of moprolol or of a pharmaceutically acceptable salt thereof.

* * * * *